(12) United States Patent
Decker (10) Patent No.: US 11,364,008 B2
(45) Date of Patent: Jun. 21, 2022

(54) IMAGE COMPRESSION FOR X-RAY IMAGING DEVICES

(71) Applicant: Turner Imaging Systems, Inc., Orem, UT (US)

(72) Inventor: Keith Decker, Pleasant Grove, UT (US)

(73) Assignee: Turner Imaging Systems, Inc., Orem, UT (US)

( * ) Notice: Subject to any disclaimer, the term of this patent is extended or adjusted under 35 U.S.C. 154(b) by 70 days.

(21) Appl. No.: 16/588,410

(22) Filed: Sep. 30, 2019

(65) Prior Publication Data
US 2021/0093265 A1  Apr. 1, 2021

(51) Int. Cl.
  *A61B 6/00* (2006.01)
  *A61B 6/03* (2006.01)
  *G16H 30/40* (2018.01)

(52) U.S. Cl.
  CPC .............. *A61B 6/563* (2013.01); *A61B 6/032* (2013.01); *A61B 6/4225* (2013.01);
  (Continued)

(58) Field of Classification Search
  CPC ................... G16H 30/20; G16H 30/40; H04N 2201/33357; G06T 2207/10116
  See application file for complete search history.

(56) References Cited

U.S. PATENT DOCUMENTS 5,177,775 A  1/1993  Onodera et al.
5,482,043 A  1/1996  Zulauf
(Continued)

FOREIGN PATENT DOCUMENTS

CN  103705260 A  4/2014
CN  106388842 A  2/2017
(Continued)

OTHER PUBLICATIONS https://www.pleora.com/sites/default/files/published-articles/real_time_vid_mar2017.pdf.
(Continued)

*Primary Examiner* — Dani Fox
*Assistant Examiner* — Soorena Kefayati
(74) *Attorney, Agent, or Firm* — Kenneth E. Horton; Barnes & Thornburg LLP (57) ABSTRACT

Image compression techniques and image handling and display methods that can be used with imaging devices, including X-ray devices, are described in this application. In particular, this application describes a real-time imaging method by providing a portable x-ray imaging device containing an internal power source and an internal power supply, capturing a first x-ray image using the x-ray imaging device, compressing the first x-ray image using a compression process performed by a processor located within the portable x-ray imaging device and then wirelessly transmitting the compressed first x-ray image to a display device, capturing a second x-ray image using the x-ray imaging device, compressing the second x-ray image using the processor and then wirelessly transmitting the compressed second x-ray image to the display device; and then displaying the first and second x-ray images on the display device at a frame rate of more than about 8 frames per second.

23 Claims, 9 Drawing Sheets

(52) U.S. Cl.
CPC ........... *A61B 6/4007* (2013.01); *A61B 6/4405* (2013.01); *A61B 6/4441* (2013.01); *G06T 2207/10116* (2013.01); *G16H 30/40* (2018.01); *H04N 2201/3283* (2013.01)

(56) References Cited

U.S. PATENT DOCUMENTS

| | | | |
|---|---|---|---|
| 6,142,946 A | 11/2000 | Hwang et al. | |
| 6,210,327 B1 | 4/2001 | Brackett et al. | |
| 6,231,510 B1 | 5/2001 | Negrin et al. | |
| 6,351,547 B1 * | 2/2002 | Johnson | G16H 30/20 709/236 |
| 6,468,217 B1 * | 10/2002 | Fazioli | H04N 5/772 600/443 |
| 6,569,097 B1 | 5/2003 | McMorrow et al. | |
| 6,643,405 B1 * | 11/2003 | Sako | H04N 1/33307 375/E7.181 |
| 6,690,386 B2 | 2/2004 | Edelson et al. | |
| 6,780,154 B2 | 8/2004 | Hunt et al. | |
| 6,855,113 B2 | 2/2005 | Amemiya et al. | |
| 7,139,417 B2 * | 11/2006 | Nicolas | A61B 8/565 382/232 |
| 7,257,158 B1 * | 8/2007 | Figueredo | H04N 19/70 600/437 |
| 7,257,832 B2 * | 8/2007 | Beane | G16H 30/20 725/105 |
| 7,331,925 B2 | 2/2008 | McMorrow et al. | |
| 7,360,948 B2 | 4/2008 | RaZZano et al. | |
| 7,406,150 B2 | 7/2008 | Minyard et al. | |
| 7,418,480 B2 | 8/2008 | Katsman et al. | |
| 7,549,961 B1 | 6/2009 | Hwang | |
| 7,787,014 B2 | 8/2010 | Serceki | |
| 7,809,400 B1 * | 10/2010 | Hwang | G16H 30/20 455/418 |
| 7,905,834 B2 * | 3/2011 | Watanabe | A61B 8/565 600/437 |
| 7,920,732 B2 | 4/2011 | Shimizu et al. | |
| 7,996,495 B2 | 8/2011 | Dekel et al. | |
| 8,035,685 B2 | 10/2011 | Jensen | |
| 8,147,414 B2 | 4/2012 | Abraham | |
| 8,195,937 B2 * | 6/2012 | Wise | H04N 1/00209 713/164 |
| 8,199,685 B2 | 6/2012 | Hwang | |
| 8,275,835 B2 | 9/2012 | Eguchi | |
| 8,366,608 B2 | 2/2013 | Mitsuhashi | |
| 8,396,804 B1 * | 3/2013 | Dala | G16H 80/00 380/231 |
| 8,526,573 B2 | 9/2013 | Ferro, Jr. | |
| 8,571,280 B2 * | 10/2013 | Mathew | G16H 40/67 382/128 |
| 8,600,299 B2 | 12/2013 | Randall et al. | |
| 8,682,953 B2 | 3/2014 | Wedel | |
| 8,855,691 B2 | 10/2014 | Kamiya et al. | |
| 9,092,556 B2 | 7/2015 | Amble et al. | |
| 9,197,899 B2 * | 11/2015 | Hiriyannaiah | H04N 19/164 |
| 9,198,271 B2 | 11/2015 | Miyachi | |
| 9,258,464 B2 * | 2/2016 | Ohta | H04N 5/32 |
| 9,295,444 B2 * | 3/2016 | Schwartz | A61B 8/4483 |
| 9,402,592 B2 | 8/2016 | Garcia et al. | |
| 9,402,601 B1 | 8/2016 | Berger et al. | |
| 9,462,991 B2 | 10/2016 | Ferro, Jr. | |
| 9,525,886 B2 * | 12/2016 | Lee | G16H 50/20 |
| 9,582,055 B2 | 2/2017 | De Jong et al. | |
| 9,678,702 B2 | 6/2017 | Rust et al. | |
| 9,713,455 B2 | 7/2017 | Garcia et al. | |
| 9,763,644 B2 | 9/2017 | Pelissier et al. | |
| 9,801,616 B2 | 10/2017 | Wallack et al. | |
| 9,808,218 B2 | 11/2017 | Tezuka et al. | |
| 9,820,658 B2 | 11/2017 | Tran | |
| 9,836,654 B1 | 12/2017 | Alvi et al. | |
| 2003/0031353 A1 * | 2/2003 | Baertsch | A61B 6/00 382/132 |
| 2003/0035584 A1 * | 2/2003 | Nicolas | G06T 7/0012 382/232 |
| 2003/0190067 A1 * | 10/2003 | Tsujii | G16H 50/30 382/181 |
| 2004/0030585 A1 * | 2/2004 | Sariel | G16H 40/67 705/3 |
| 2006/0122482 A1 | 6/2006 | Mariotti et al. | |
| 2008/0020332 A1 * | 1/2008 | Lavenda | A61B 6/4488 430/495.1 |
| 2008/0232718 A1 * | 9/2008 | Avinash | A61B 6/563 382/305 |
| 2009/0028401 A1 * | 1/2009 | Tanabe | A61B 6/4494 382/128 |
| 2009/0304254 A1 * | 12/2009 | Yoshida | A61B 6/00 382/132 |
| 2010/0191094 A1 * | 7/2010 | Bowers | A61B 5/0013 600/437 |
| 2010/0202510 A1 | 8/2010 | Kyle | |
| 2011/0275924 A1 * | 11/2011 | McLellan | G16H 30/20 600/407 |
| 2012/0324397 A1 * | 12/2012 | Patz | G16H 40/67 715/764 |
| 2013/0039549 A1 * | 2/2013 | Muller | G01R 33/543 382/128 |
| 2013/0076747 A1 * | 3/2013 | Koenig | A61B 6/5223 345/419 |
| 2013/0336552 A1 * | 12/2013 | Sehnert | A61B 6/487 382/128 |
| 2014/0050418 A1 * | 2/2014 | Liu | A61B 6/563 382/270 |
| 2014/0267330 A1 * | 9/2014 | Sproul | A61B 8/12 345/522 |
| 2015/0172681 A1 * | 6/2015 | Kim | G16H 30/40 382/128 |
| 2015/0223767 A1 * | 8/2015 | Sehnert | A61B 6/547 378/42 |
| 2017/0347056 A1 * | 11/2017 | Kurita | A61B 8/5207 |
| 2018/0108447 A1 * | 4/2018 | Turner | A61B 6/4452 |
| 2019/0015057 A1 * | 1/2019 | Diaz Carmena | A61B 6/4411 |

FOREIGN PATENT DOCUMENTS

| | | |
|---|---|---|
| JP | 2012176087 A | 11/2015 |
| KR | 1020150044168 A | 10/2015 |

OTHER PUBLICATIONS http://www.ndssi.com/medical-monitors-visualization-products/hd-wireless-medical-monitor-devices.html.
http://www.auntminnie.com/index.aspx?sec=ser&sub=def&pag=dis&ItemID=110241.
https://www.synergymedco.com/product/nds-surgical-imaging-zerowire-g2-wireless-imaging/.
https://www.konicaminolta.com/medicalusa/product/imagepilot-aero-3/.
https://www.konicaminolta.com/medicalusa/product/aerodr-retro-fit-portable-solution/.

* cited by examiner

IMAGE COMPRESSION FOR X-RAY IMAGING DEVICES

FIELD

This application relates generally to imaging equipment. More specifically, this application relates to image compression, video compression, image handling, and wireless transmission techniques that can be used with medical x-ray imaging equipment, especially portable x-ray imaging devices.

BACKGROUND

X-ray imaging systems typically contain an X-ray source and an X-ray detector. The X-ray detector is often an image intensifier or even a flat panel digital detector. X-ray imaging systems are often configured as a C-arm assembly with the source and detector on opposite ends of the "C" arm. The C-arm assembly can move through continuous rotation angles relative to the object in order to acquire images from multiple orientations.

Medical X-ray imaging equipment, especially when configured as a C-arm, is traditionally heavy and cumbersome to move and position in order to obtain the desired patient images within the operating room environment. Because the equipment is heavy, and draws significant electrical power, it has not been possible to make the devices light enough and small enough to be portable, hand-carried, and/or hand-operated. Advances in many technologies associated with X-ray systems are changing this situation and opening up new applications and much greater ease of use than before. These new applications and greatly improved ease of use also stimulates the need for a new way to handle the image data that is generated in obtaining x-ray images using a portable or hand-held system.

SUMMARY

This application relates generally to image compression techniques and image handling and display methods that can be used with imaging devices, including X-ray devices. In particular, this application describes a real-time imaging method that comprises providing a portable x-ray imaging device containing an internal power source and an internal power supply, capturing a first x-ray image using the x-ray imaging device, compressing the first x-ray image using a compression process performed by a processor located within the portable x-ray imaging device and then wirelessly transmitting the compressed first x-ray image to a display device, capturing a second x-ray image using the x-ray imaging device, compressing the second x-ray image using the processor and then wirelessly transmitting the compressed second x-ray image to the display device; and then displaying the first and second x-ray images on the display device at a frame rate of more than about 8 frames per second. The application also relates to a hand-held X-ray imaging device, comprising a support arm with a housing enclosing an internal power supply and an internal, removable power source, the power source being replaceable and delivering 60 or more X-ray images using a single charge, the support arm being configured to rotate around an object to be analyzed while being held by a support structure, an X-ray source contained near one end of the support arm, an X-ray detector contained near the other end of the support arm, an internal processor and supporting electronics configured to compress an x-ray image and wirelessly transmit the compressed x-ray image to an external display device, and a trigger configured to be to be activated by hand after the imaging device is properly positioned, wherein the x-ray device is configured to be removable from the support structure and used in a stand-alone fashion for x-ray imaging. These devices and methods can deliver a fluoroscopy image sequence at a high frame rate while not losing the image quality required by the surgeon or radiologist, where the last image is often given a more in-depth analysis by the user (i.e., a surgeon or radiologist).

BRIEF DESCRIPTION OF THE DRAWINGS

The following description can be better understood in light of the Figures which show various embodiments and configurations of the image compressions techniques and image handling and display methods that can be used with portable X-ray devices.

Together with the following description, the Figures demonstrate and explain the principles of the structures, methods, and principles described herein. In the drawings, the thickness and size of components may be exaggerated or otherwise modified for clarity. The same reference numerals in different drawings represent the same element, and thus their descriptions will not be repeated. Furthermore, well-known structures, materials, or operations are not shown or described in detail to avoid obscuring aspects of the described devices.

DETAILED DESCRIPTION

The following description supplies specific details in order to provide a thorough understanding. Nevertheless, the skilled artisan will understand that the described data and image compression, image handling, video and image display, and data transmission techniques can be implemented and used without employing these specific details. Indeed, the described systems and methods for controlling X-ray devices and displaying images and video obtained by these devices can be placed into practice by modifying the described systems and methods and can be used in conjunction with any other imaging apparatus or imaging techniques. For example, while the description below focuses on data and image compression, imaging handling, video and image display, and data transmission as applied to C-arm x-ray devices, other X-ray imaging arms and x-ray devices can be used, including U-arms or portable x-ray devices with separate detectors that are configured to approximate the C-arm configuration. In addition to X-ray imaging, the method may be employed with any medical imaging device such as ultrasound or nuclear magnetic resonance (NMR) wherein a sequence of images is captured on one component and transferred to a separate image display component by wireless protocol using a lossless or lossy compression algorithm and similar techniques and methods for transmitting the compressed and subsequently the uncompressed image or video data.

In addition, as the terms on, disposed on, attached to, connected to, or coupled to, etc. are used herein, one object (e.g., a material, element, structure, member, etc.) can be on, disposed on, attached to, connected to, or coupled to another object—regardless of whether the one object is directly on, attached, connected, or coupled to the other object or whether there are one or more intervening objects between the one object and the other object. Also, directions (e.g., on top of, below, above, top, bottom, side, up, down, under, over, upper, lower, lateral, orbital, horizontal, etc.), if provided, are relative and provided solely by way of example and for ease of illustration and discussion and not by way of limitation. Where reference is made to a list of elements (e.g., elements a, b, c), such reference is intended to include any one of the listed elements by itself, any combination of less than all of the listed elements, and/or a combination of all of the listed elements. Furthermore, as used herein, the terms a, an, and one may each be interchangeable with the terms at least one and one or more.

FIGS. 1-7 show some embodiments of the portable X-ray devices 100. The X-ray devices 100 contain an imaging arm (or support arm) that allows the system to be used to take X-ray images of a portion of a patient's body or any other object capable of being analyzed by x-rays, including animals, industrial components such as electronic circuit boards, containers to be inspected, and/or passenger luggage. In some configurations, the imaging arm is substantially shaped like the letter "C" and is therefore referred to as a C-shaped support arm (or C-arm) 105. The C-arm has any size that can be held and operated by hand when in use, as seen in FIG. 1A or 1B. In some configurations, the x-ray devices 100 can be hand-held so they can be carried by hand and/or operated by hand.

The C-arm 105 can contain any X-ray source 135 and X-ray detector 140 that allow the X-ray device 100 to take X-ray images. The X-ray source 135 can contain any source that generates and emits X-rays, including a standard stationary anode X-ray source, a micro-focus x-ray source, a rotating anode x-ray source, and/or a fluoroscopic X-ray source. In some embodiments, the x-ray source 135 can operate with about 40 to about 90 kV and from about 1 to about 10 mA. In other embodiments, the x-ray source can operate with about 70 KV to about 120 KV and from 1 to about 15 mA. In still other embodiments, the x-ray source can operate with about 75 kV and about 2 mA. In some configurations, the X-ray source and x-ray detector can be made modular so that different sizes and types of X-ray sources and x-ray detectors can be used in the x-ray device 100.

The X-ray detector 140 can contain any detector that detects X-rays, including an image intensifier, a CMOS camera and/or a digital flat panel detector. In some configurations, the detector can have a substantially square shape with a length ranging from about 13 cm to about 15 cm. In other configurations, though, the x-ray detector 140 does not need to have a substantially square shape. In addition, the x-ray detector can have a pixel size that ranges from a square with dimension ranging from about 25 µm to about 200 µm, to a rectangle with the two dimensions of the rectangular pixel fitting in about the same range.

In some configurations, the detector can have a substantially square shape with a length of one side ranging from about 13 cm to about 15 cm. In other configurations, the detector can have a substantially rectangular shape with the shorter dimension ranging from 12 cm to 16 cm, and the longer dimension ranging from 18 cm to 24 cm. The X-ray source 135 can be contained in a housing that can be configured in two parts with a first part enclosing the x-ray source 135 and a second, separate part enclosing the x-ray detector 140. In other configurations, however, the housing can be configured so that it is a single part that encloses both the X-ray source 135 and the X-ray detector 140.

In some configurations, the housing 155 can also enclose a removable power source (such as a battery) and optionally an internal power supply. Thus, the power source and the power supply can be located internal to the housing 155 and also to the x-ray device 100. The supporting electronics for the power source and the power supply, as well as the supporting electronics for an image display and for wireless data upload, can also be located internal to the housing 155. Thus, in these configurations, the x-ray device 100 does not contain an external power cord or data cable. Incorporating the removable power source (i.e., the battery), the power supply, and the supporting electronics all within the housing allows the size and the weight of the device 100 to be reduced. With such a configuration, the power source can easily be replaced and delivers 60, 80, 100, 120, or even more x-ray images using just a single charge, with the exact number of images obtained with a single power source depending on the voltage and current parameters required for the images taken with a higher power setting reducing the number of images that can be obtained. Of course, if needed, the x-ray device 100 can be configured so that it is alternately, or additionally, charged using external power from a power cord that is plugged into a wall outlet. In other configurations, multiple power supplies can be provided for the source, detector, and control electronics, any (or all) of which can be located either internal or external to the housing 155.

Figure 1A:
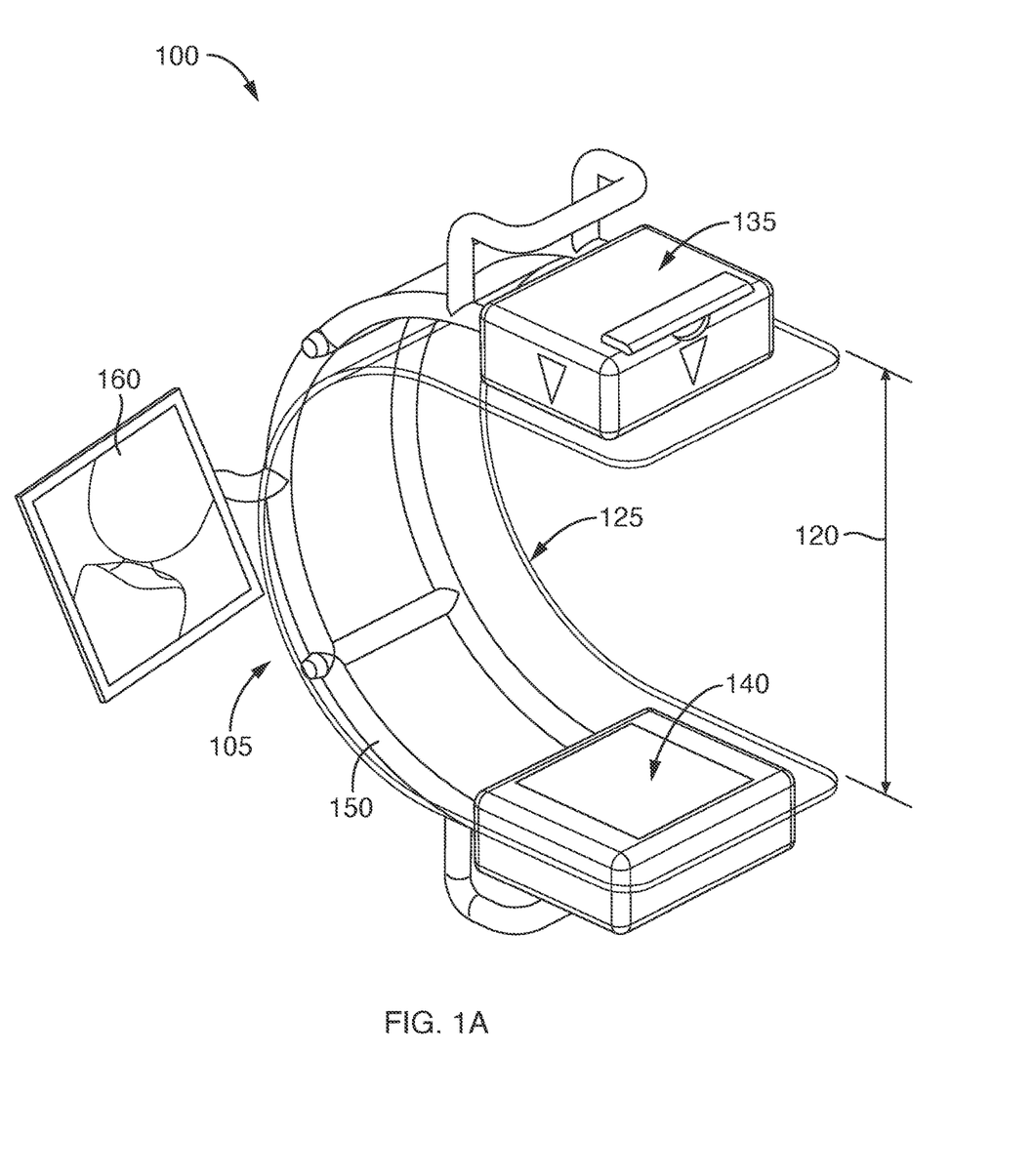
FIGS. 1A and 1B shows a view of some embodiments of small, portable X-ray devices.
Figure 1B:
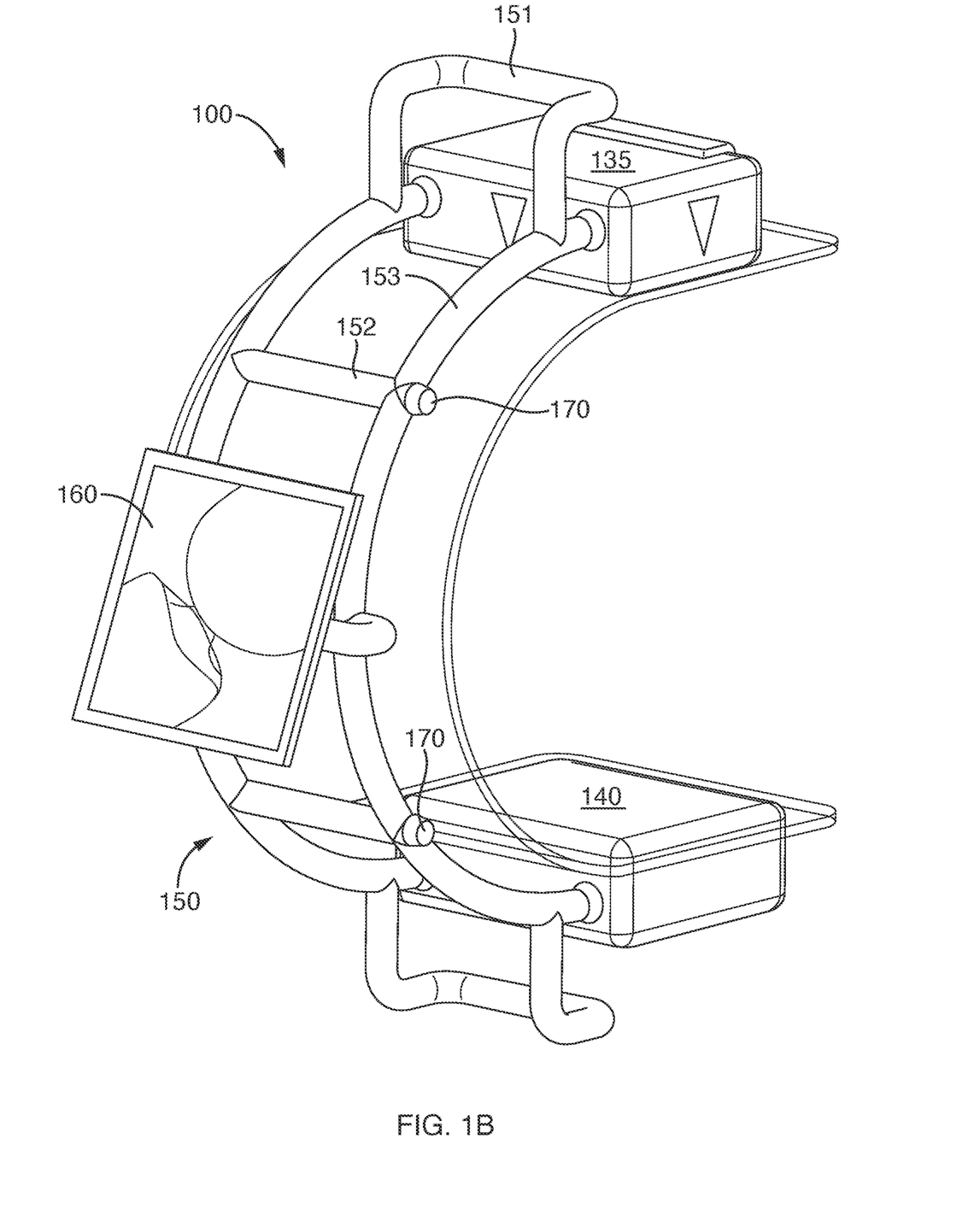

In some instances, the X-ray device 100 contains a frame 150 that has an open configuration. As shown in FIGS. 1A and 1B, an open configuration gives a number of easy gripping options for a user to carry and hold the frame 150 during transport, and optionally during operation of the x-ray device 100. In some embodiments, the frame 150 can be configured as a modular unit so different cross members (or length member or handles) can be used to replace the existing cross members (or length member or handles). Thus, the frame 150 provides the ability for a user (or operator) to grip and hold the X-ray device 100 during operation, a feature that is useful since some other conventional C-arms can't be held in the hands while being operated because they do not have a suitable frame and because they are too heavy.

The x-ray device 100 can be activated by a trigger located anywhere on the x-ray device 100 that can be activated easily by the user. For example, the trigger could be activated near locations 151, 152, 153, and/or 170 on the C-arm. In other configurations, a separate foot switch that communicates with the x-ray device 100 using a wired or Bluetooth/wireless connection can be used. Indeed, the portable x-ray device 100 could be equipped with both a trigger on the device as well as a foot switch. The operation of any one of the triggers and/or the foot switch can also activate the image compression/decompression, handling, and video/image display functions both contained within the x-ray device 100 and on the separate image display device or tablet. In this manner, the surgeon, radiologist, medical practitioner, or other user can simultaneously control the manner in which the x-ray images are obtained by holding or guiding the x-ray device 100 while viewing the results obtained from the imaging on a conveniently-located display. This is one of the features enabled by the x-ray device 100. The ability to easily guide or manipulate the x-ray device 100 by hand while simultaneously viewing the image results enables the medical practitioner to obtain the x-ray images or video information needed to support the desired medical procedure in a manner similar to the way digital still and video cameras in cell phones and other personal electronic devices have enabled new and more effective ways to document, communicate, use, and share visual information. These configurations thus enable quicker and better medical decisions and encourage more frequent imaging "snapshots" during medical procedures which will lead to medical practitioners acting on better information, with the final result being better medical outcomes for the patient.

Figure 2:
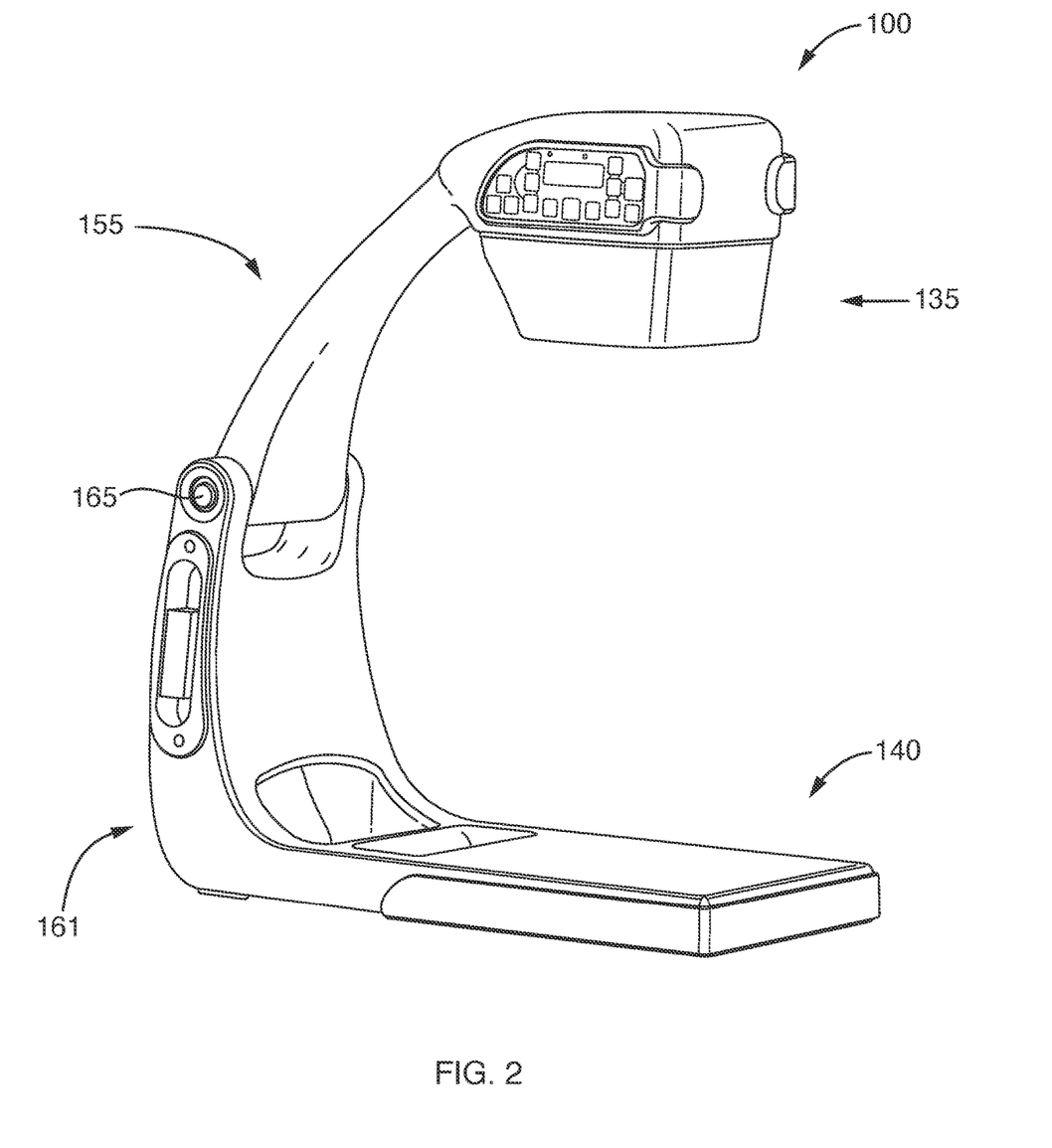
FIG. 2 shows another view of some embodiments of small, portable X-ray devices.

In other embodiments, the portable x-ray device 100 has the configuration illustrated in FIG. 2. In FIG. 2, the frame 150 has a first portion 156 that is part of the housing 155 that contains the x-ray source 135 and the associated electronics. The frame 150 also has a second portion 161 that is part of the housing 155 that also contains the x-ray detector 140 and the associated electronics. The first portion 156 of the housing and the second portion 161 of the housing are connected using hinge 165. The bottom of the portable x-ray device can contain an opening 175 that can be used when attaching the x-ray device 100 to an external support structure.

The portable x-ray device 100 has several features not exhibited by other C-arm devices. First, it has the capability of wireless data transfer, thereby eliminating the need for any wired connections or cables to the C-arm 105 or imaging arm. Second, it is internally powered by a removable battery or internal power source and, therefore, more portable than other C-arm devices which require a power cable. Third, it is lighter than other C-arm devices. As a comparison, the portable x-ray devices 100 described herein can have a weight ranging from about 10 to about 25 pounds while other C-arm devices have a weight ranging from about 35 to about 375 pounds. In other embodiments, the portable x-ray C-arm devices 100 described herein can have a weight ranging from about 12 to about 18 pounds.

Figure 3A:
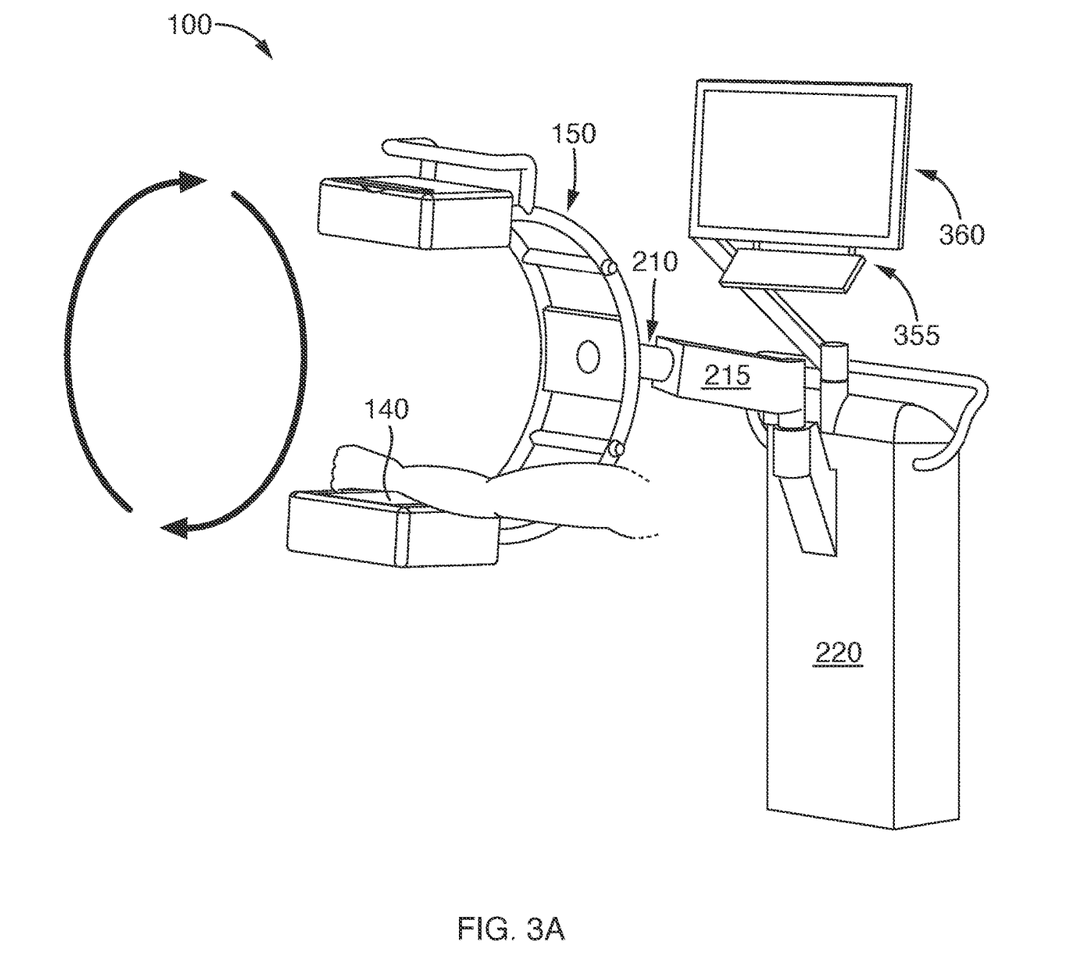
FIGS. 3A and 3B show some methods of using small, portable X-ray devices in an operating room.
Figure 3B:
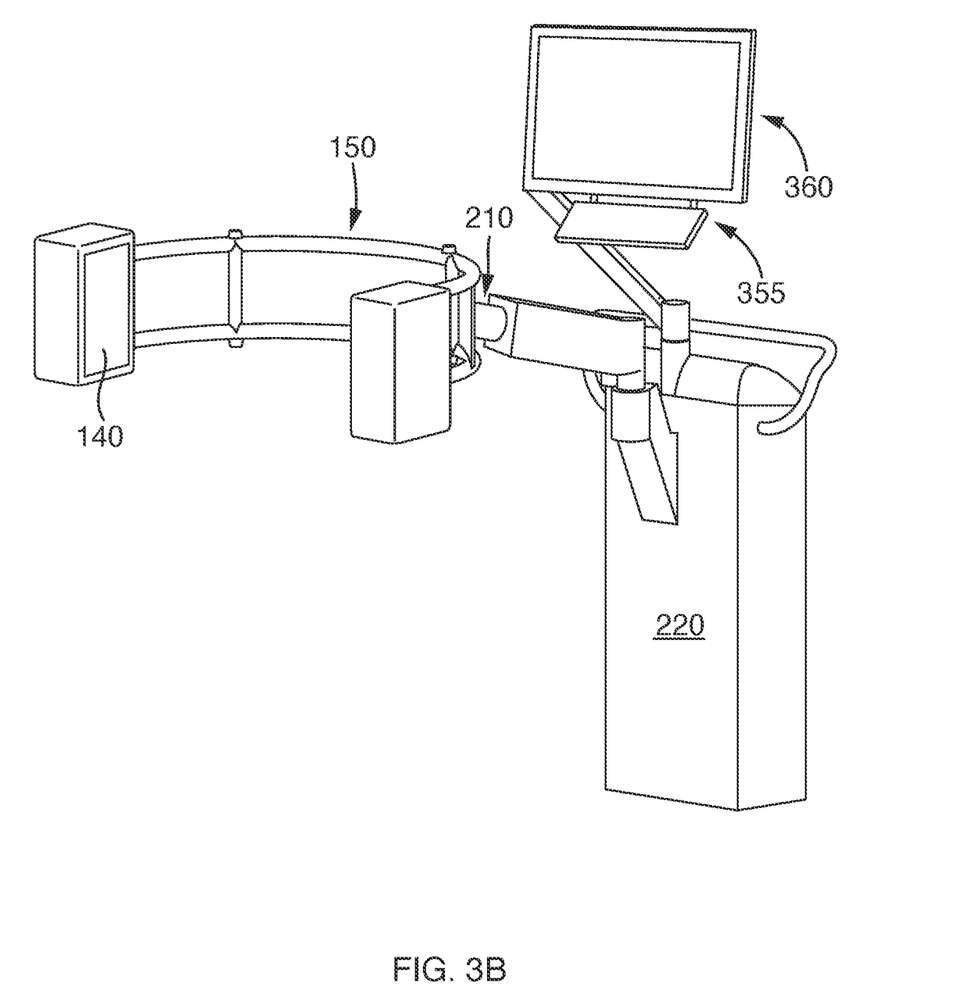
Figure 4:
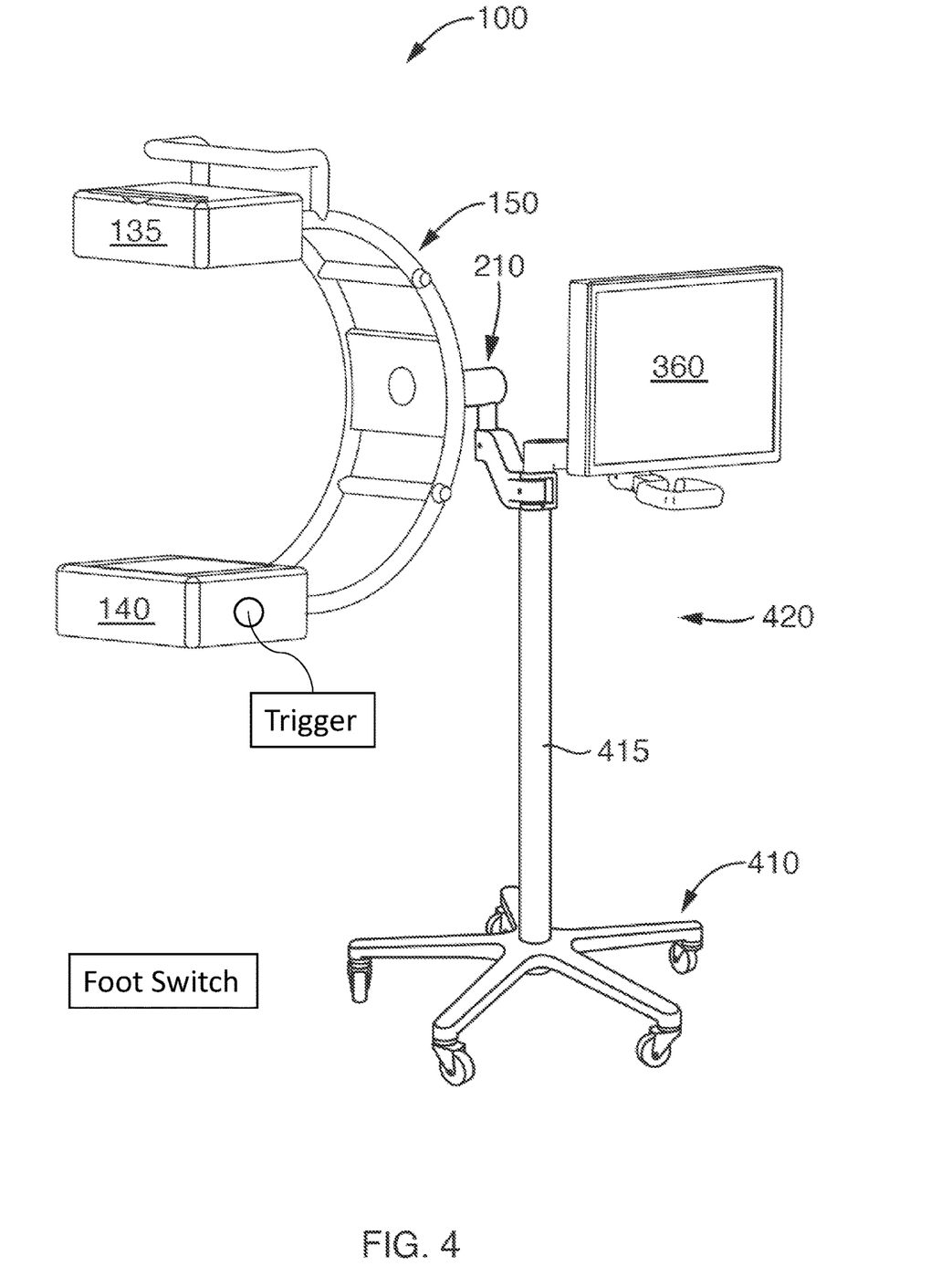
FIG. 4 shows some embodiments of small, portable X-ray devices being connected to a wheeled support structure.
Figure 5:
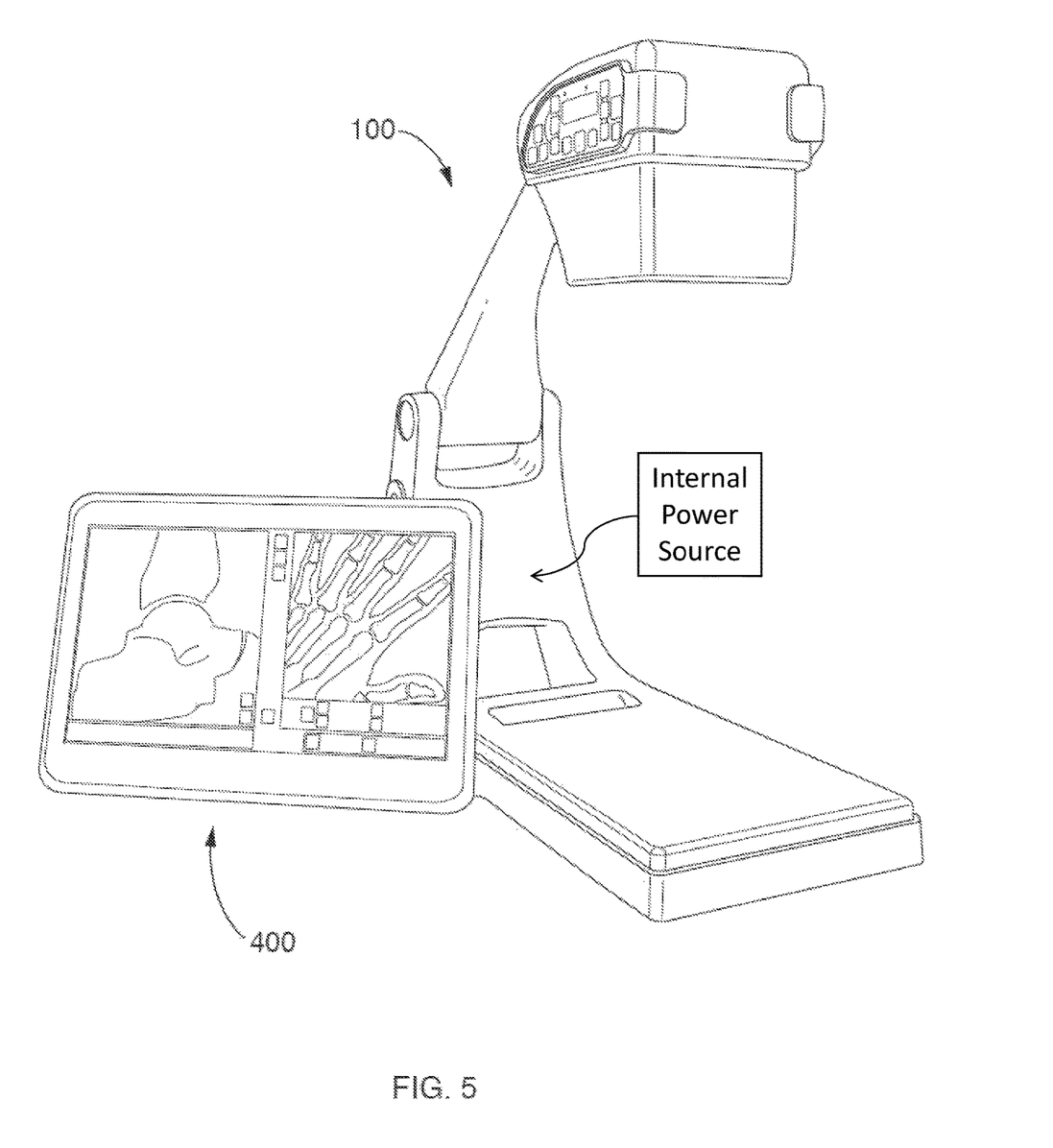
FIG. 5 shows some embodiments of x-ray systems containing portable x-ray devices and an external electronic device for displaying the x-ray image(s).

In some configurations, the portable x-ray device 100 can be connected to a stationary external (or support) structure so that it can rotate, or be positioned, around an object being analyzed, as shown in FIGS. 3A and 3B and as described in U.S. patent application Ser. No. 15/568,708, filed Nov. 23, 2017, the entire disclosure of which is incorporated herein by reference. This support structure contains a base 220, arm 215, tri-joint 210, input/output interface 355, and display device 360. In other embodiments, the portable x-ray device 100 can be connected to a mobile external (or support) structure for a similar purpose, as shown in FIG. 4 and as described in U.S. patent application Ser. No. 16/198,956, filed Nov. 23, 2018, the entire disclosure of which is incorporated herein by reference. Attaching the portable x-ray device to a support structure allows the operator to position the portable x-ray device 100 as needed for a series of imaging procedures, while freeing medical personnel to attend to other duties. As well, it leaves the hands of the operator free for other actions. For example, during a surgical procedure, attaching the portable x-ray device 100 to a support structure allows the medical person to take many actions, but then easily image the patient when needed using the pre-selected positioning of the portable x-ray device 100. When the surgical procedure is complete, the portable x-ray device 100 can be removed from the support structure and taken to another location for use or storage.

In other configurations, though, the portable x-ray device 100 can be connected to a movable support structure. In such configurations, the movable support structure can be configured to move across a floor while supporting the x-ray device 100. Thus, the movable support structure can comprise one or more wheels, shelves, handles, monitors, computers, stabilizing members, limbs, legs, struts, cables, and/or weights (to counterbalance the weight of the imaging arm and/or any other component and prevent tipping the movable support structure). FIG. 4 shows some embodiments in which the movable support structure 420 comprises a wheeled structure 410 connected to a stand 415 that contains a tri joint 210 that is connected to the x-ray device 100.

In some configurations, the X-ray device 100 and/or the external support structure can comprise any suitable locking mechanism that can selectively lock and unlock the rotation of the C-arm 105 around the object being analyzed. For instance, the locking mechanism can comprise a manually-engaged clamp, a detent mechanism, a motorized lock, an electric lock, a radio controlled lock, a remotely engaged clamp, and/or any other suitable mechanism that can be used to lock and release the orbital rotation of the c-arm. In some configurations, the locking mechanism can be part of the tri joint described herein or even an interface between the x-ray device 100 and the tri joint 210.

The x-ray device 100 can also be connected to any type of electronic device with a wireless or a wired connection. In these embodiments, the portable x-ray device 100 itself can analyze, process, and/or transmit image or video data to the desired electronic device, (such as a desktop computer, laptop computer, tablet, cellphone, etc. . . . ), which can be used to view the x-ray images and, in some configurations, further analyze the x-ray images from the x-ray detector. In other embodiments, however, the x-ray detector 140 can be connected with any wireless communications device that can be paired with the desired electronic device, such as tablet 200 shown in FIG. 5.

In some embodiments, the X-ray detector and the X-ray source can be mounted and located separately, as is common with medical x-ray systems that are not C-arm devices, including wall-mounted or ceiling-mounted x-ray devices. In these embodiments, the x-ray source may optionally be battery powered, while the digital flat-panel x-ray detector can be battery powered and will communicate with the desired electronic device (containing a display) via wireless communications technology, similar to the embodiments described herein. Separating the X-ray source and the X-ray detector in this manner will allow for flexibility in positioning the patient or the patient's body part that needs to be examined by x-ray imaging, while the use of the battery-powered digital flat panel x-ray detector with wireless data communications provides the benefits of no data or power cables, ease of positioning, and ease of transportation in use.

During imaging, the x-ray detector operation should be coordinated with the operation of the x-ray source. The x-ray source and the x-ray detector must both be ready for operation when the x-ray source is energized in order to avoid the possibility of irradiating the patient with ionizing radiation when the imaging system is not ready to capture an image. If this were to occur, the patient would be potentially harmed by the ionizing radiation with no compensating medical benefit from the desired x-ray images.

There are several ways this coordination can be implemented. In the configurations when the x-ray source and the detector are separated (and not configured into a C-arm), the coordination can be performed through wireless communication. In the configurations where the flat panel x-ray detector is operated in a continuous read-out mode and the x-ray source is continuously operated, this coordination can be accomplished using a simple "on" and "off" signal to the x-ray source and the detector simultaneously.

In the configurations that use pulsed x-ray operation, the x-ray source and the detector should be coordinated more carefully. Pulsed x-ray operation can often be used for fluoroscopy, or for stop-motion x-ray radiography, and provides benefits of higher instantaneous x-ray intensity or power to the imaging detector (for a given time-averaged x-ray intensity or total dose). Therefore, less quantum noise and a better signal-to-noise ratio in the image is produced, as well as other image quality benefits for a given total x-ray dose to the patient. The detector that is used in such a configuration will typically require some amount of time (typically measured in milliseconds or less) to readout an image before it can be ready to receive x-ray irradiation and capture a new image. Therefore, the x-ray detector will typically provide a "ready" signal to tell the x-ray source to produce the x-ray radiation. In order to produce a fluoroscopic image with a significant number of sequential x-ray images per second (typically at least as many as 8 per second up to 30 per second or more), this coordination between the x-ray source and the flat-panel x-ray detector can occur rapidly and repeatedly many times per second, with a typical time between x-ray pulses ranging from about 100 milliseconds for a rate of about 10 frames per second, down to about 30 milliseconds for a rate of about 30 frames per second.

Figure 7:
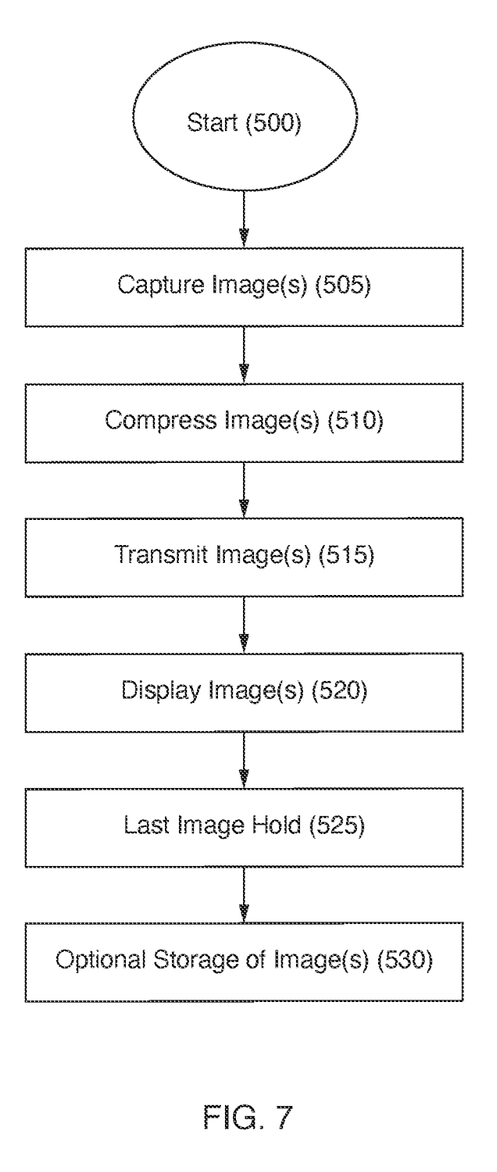
FIG. 7 shows additional embodiments of imaging methods that compress and decompress images for display.

The portable x-ray devices 100 can be used in substantially real-time methods of displaying images to the operator of the device, as shown in FIG. 7. In real-time methods, the x-ray images are being observed as they occur with only a slight delay between the image being taken and being displayed, with the intent to make the delay as small as practicable. With the x-ray devices 100 configured as described herein, that delay can be minimized to an almost imperceptible time period which can be attributed to a response time. In the x-ray devices 100, the response time from the trigger activation to the first image appearing can be about 500 ms, 600 ms, 700 ms, 800 ms, or about 900 ms. Once initiated, each subsequent image frame will appear to the operator with approximately this same time lag from the moment that it was initially captured by exposure of the detector to x-rays. With the response time under a second, as described, this time lag is only marginally perceptible to the operator and the performance is acceptable to the medical practitioner. However, in some instances, this response time can be about 1, about 1.5, about 2, about 3, or even about 5 seconds, depending on the operator, the capability of the x-ray device, and the medical procedure. In other embodiments, the response time can be any combination or subcombination of these time periods.

These imaging methods start at box 500 when the device 100 is triggered. In box 505, the device 100 captures an image or series of images. The imaging detector(s) of the x-ray device 100 captures the x-ray image(s) as a frame or a sequence of frames that can form part of or an entire video sequence. The number of frames per second (FPS) or the number of images per second is known as the frame rate. In some embodiments, the x-ray device 100 can then transmit that data at a particular frame rate to an external computer (or other electronic device) for processing or to a display device for displaying to a user or operator of the imaging device.

For proper communication between the flat panel digital detector and the x-ray source, the x-ray radiation power, x-ray intensity, and possibly other x-ray exposure parameters can be adjusted as the fluoroscopic image sequence progresses. These conditions can be adjusted in both the C-arm configuration or a structurally unattached detector. While it is common to set approximate exposure parameters based on the type of x-ray image to be obtained, with a larger or denser body part requiring a higher exposure power than a smaller or less dense body part, such approximate exposure settings do not always guarantee an optimum image quality. Therefore, in some configurations, it is helpful to provide an algorithm in the imaging system, whether the algorithm is implemented in the detector, or in the display device, or elsewhere as desired by the designer, that analyzes the brightness and contrast of the initial image or first few images obtained and adjusts the x-ray exposure, and the detector sensitivity and other parameters, to obtain an optimum image. This algorithm should rapidly approach the optimum exposure in order to minimize the patient dose. This type of image-adjusting algorithm is often called an Automatic Brightness or Auto Exposure Control and is often used to compensate the exposure settings when metal (such as a screw or a pin) or other x-ray dense material, is present in the body part being imaged, because an x-ray dense material will block the x-rays from reaching the detector and create a region in the image that is significantly different from the average brightness in the image. This region of anomalous brightness can cause the over-all image to appear over or under exposed without proper compensation.

In some embodiments, an automatic brightness stabilization (or ABS) technique can be used during the imaging method. In order to be useful, the ABS technique must function rapidly (converging to an acceptable result within about 10 frames or less) in order to stabilize the x-ray source operating parameters of voltage and current that provide a proper exposure on the detector and therefore an acceptable image brightness. The ABS method compares the anatomy being imaged to a reference, i.e., an acrylic glass or poly (methyl methacrylate) (PMMA) material thickness that was pre-imaged and adjusted to proper brightness during development of the x-ray device 100. The x-ray detector's average pixel intensity and the x-ray source kV/mAs, are measured for varying thicknesses of PMMA. With this data, a lookup table can be created so that any anatomy under examination can be compared to an equivalent reference PMMA thickness. After knowing the equivalent PMMA thickness, the x-ray source kV and mAs can be quickly determined based on a second PMMA thickness to anatomy lookup table that provides the recommended x-ray source settings for the anatomy being imaged.

The methods in FIG. 7 continue when the x-ray images are transmitted, as shown in box 515. In some embodiments, transmission of the images can be performed using a wireless protocol since the x-ray device (or just the flat panel detector) is portable and has no physical connections to a display device, computer, medical data storage system, or other electronic device. Using a lower speed connection like a wireless Wi-Fi protocol, however, can limit the number of frames per second that are transmitted. Since wireless transmission suffers from lower connection speeds relative to wired transmission, compression processes can be used to shrink the size of the image data before it is transmitted, as shown in box 510 of FIG. 7. Compression processes are widely used in the transmission of pictures and/or videos over slow bandwidth connections, including the internet and many Wi-Fi enabled devices like smart phones, tablets and laptops. As well, many media providers have been successful in providing high resolution images and movies on lower speed connections using a variety of compression techniques. Some of these compression techniques are described in U.S. Pat. No. 7,257,158, the disclosure of which is incorporated herein by reference.

In some configurations, a lossless or lossy compression process can be used. Typically, a lossless compression process does not produce as large a reduction in the amount of data associated with a given image as can be obtained using a lossy compression process. For this reason, lossy compression processes are much more commonly used to compress images and video sequences for transmission over limited band-width connections, whether wired connections or wireless.

Another compression process that can be used involves cell binning which reduces the byte size of a frame. In these embodiments, the cell binning process will take 4 pixels and average them together into 1 pixel. This binning process reduces the byte size of the frame by a factor of 4, decreases the pixel width and pixel height of the frame by a factor of 2, and decreases the quality of the image significantly. Compared to this binning process, a lossy image compression algorithm can reduce the frame byte size by a factor of 16 or more but still maintain the image pixel width and pixel height and only negligibly impact the image quality.

In a lossy compression algorithm, the number of bytes for each image frame can be reduced substantially in many instances. Reducing the byte size, or the amount of data, of each image frame will allow the frame rate to be higher and more suitable for an x-ray video imaging sequence transmitted using a given wireless protocol with a certain bandwidth. However, a lossy compression can also limit the quality of the x-ray image. Since image quality is an important performance parameter for medical imaging, it is desirable to avoid any kind of lossy compression. However, in order to achieve the desired video frame rate and provide the x-ray image data as a motion picture, which is valuable and necessary in many medical procedures, it can be necessary to compromise the image quality during the video sequence.

By using lossy or lossless data compression combined with methods of transmitting compressed images rapidly followed by the re-transmission of the same images at full uncompressed resolution, the methods described herein solve a data handling problem. This problem occurs where a fluoroscopic image sequence is needed. Fluoroscopy is the process of taking a rapid sequence of x-ray images in order to generate a motion video sequence, similar to what is done for a movie. In order to generate a useful sequence, images must be generated at a rate of at least 8 per second, with higher rates beyond this lower limit preferred. Given the level of detail required in medical x-ray imaging, the needed data transmission rate that would be required for full-resolution, uncompressed images exceed current and foreseeable wireless data transmission technology that would meet the requirements for use with portable medical devices.

Figure 6:
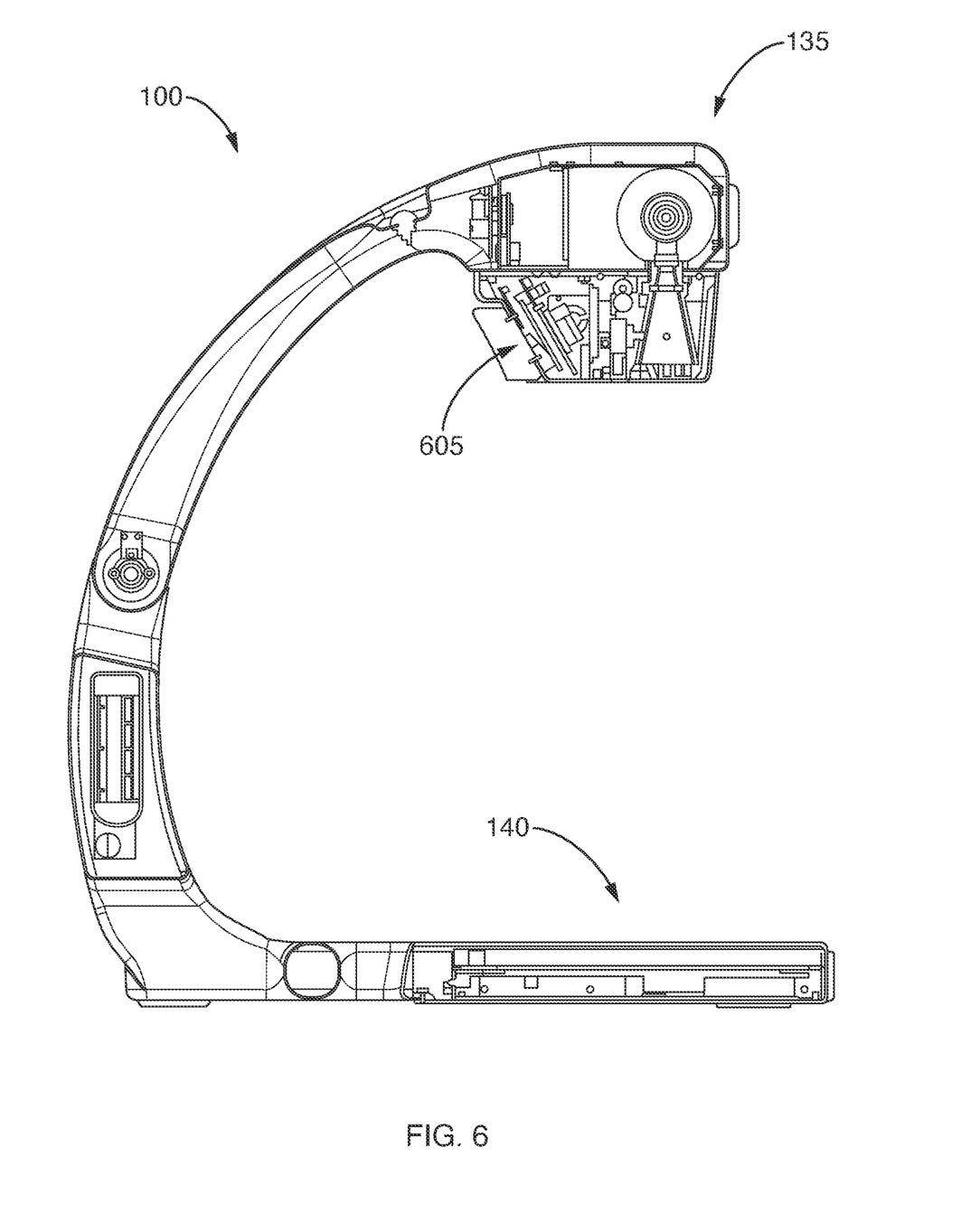
FIG. 6 shows some embodiments of small, portable X-ray devices containing an internal FPGA board.

Unlike some conventional devices, the portable x-ray device 100 can perform the desired compression process in the portable x-ray device itself rather than letting any external electronic device perform the compression. Accordingly, as shown in FIG. 6, the portable x-ray device contains an internal processor and supporting electronics that can perform this compression process. In some embodiments, the internal processor and supporting electronics are in the form of a field programmable gate array (FPGA) processor that is contained on a PCB (printed circuit board) 605. The PCB 605 can be located within the housing of the portable x-ray device 100 near the x-ray source 135. In some embodiments, the internal processor and supporting electronics are in the form of a Raspberry Pie or a similar computing device.

In some configurations, the internal processor and supporting electronics can instead be located near the x-ray detector 140. In these configurations, to make room for the internal processor and supporting electronics in the housing 155, the detector can be made thinner. The processor and supporting electronics can then be programmed to operate with the detector.

In some instances, the internal processor and supporting electronics can be used not only to compress the images, but also to improve the images before they are transmitted. One image improvement technique includes edge enhancement. Edge enhancement is an image analysis approach that seeks to enhance the "edges" of elements in the image by finding regions of quick contrast changes and altering the greyscale values of the pixels in these regions to make the "edge" more apparent to the eye. Another image improvement technique includes auto anatomy orientation which automatically orients the image for easy analysis by the surgeon, for example, by making the fingers always point up on a hand image.

The internal processor and supporting electronics can be used not only to compress the images, but also to analyze the images before they are transmitted. One image analysis technique is "auto brightness," which provides automatic exposure feedback into the C-arm system to adjust the x-ray tube current and voltage to get an optimized exposure on the detector within the first few frames.

During transmission of the images, the frame rate needs to be controlled, especially during a video or fluoroscopy sequence. Once the video sequence is completed, there is time to switch from transmitting a compressed image to an uncompressed image, thus providing access to a full resolution image at the end of the video sequence transmission. This last image of the sequence can be maintained or held on the display device (i.e., the imaging monitor) at a higher resolution to allow for more thorough clinical review, as described herein, and is called the Last Image Hold or LIH and is shown in box 525 of FIG. 7.

During the transmission and display of the image sequence, the frame rate can be controlled to balance the quality of the images with the available wireless transmission speed. A typical movie generally has a frame rate of 24 frames per second to 30 frames per second. At these frame rates, the human eye cannot easily distinguish the flicker from one frame to the next except for objects that have high rates of motion across the image field. Frame rates in this range provide a video image that looks natural or as if it has a normal motion. When the frame rate drops below about 15 frames per second, the motion can begin to look choppy or broken up even for images with very little motion from one frame to the next. When working with medical x-ray images, though, it can be acceptable to have frame rates as low as 8 frames per second depending on the requirements of the medical imaging procedure. Of course, higher frame rates can be used.

The speed at which a wireless transmission method needs to operate can be determined based on the number of bytes of data in each frame. The speed or bit rate is measured by the number of bits of data transmitted during one second or as bits per second (bps). Most wireless devices rate the speed in millions of bits per second (Mbps). Table 1 below compares the detector pixel resolution with the Wi-Fi speed needed to transmit at 8 and 30 frames per second.

TABLE 1

Comparison

| Detector Image | Pixels Width | Pixels Height | MBytes per Frame | MBits per Frame | Frames per Second | MegaBits per Second | WiFi Speed Min Mbps | WiFi Speed Max Mbps |
|---|---|---|---|---|---|---|---|---|
| Full Resolution | 1600 | 1600 | 5.1 | 41 | 30 | 1229 | 1597 | 1966 |
| Full Resolution | 1600 | 1600 | 5.1 | 41 | 8 | 328 | 426 | 524 |
| Binning 2 × 2 | 800 | 800 | 1.3 | 10 | 30 | 307 | 399 | 492 |
| Binning 2 × 2 | 800 | 800 | 1.3 | 10 | 8 | 82 | 106 | 131 |
| Compressed Image | 1600 | 1600 | | 0.300 | 30 | 9 | 12 | 14 |
| Compressed Image | 1600 | 1600 | | 0.300 | 8 | 2 | 3 | 4 |

The practical average bit rate for a Wi-Fi device is understood to be 30% to 60% of the theoretical speed or connection speed for the given wireless protocol due to the presence of signal interference and other challenges in implementing a WiFi transmission in a real-world environment. Table 2 below shows the theoretical and actual average speeds for 5 different Wi-Fi protocols.

TABLE 2

Wi-Fi Protocol Speeds

| Wi-Fi Protocol | Theoretical Speeds Mbps | Actual Average Speeds Mbps |
|---|---|---|
| IEEE 802.11b | 11 | 5.5 |
| IEEE 802.11a | 54 | 20 |
| IEEE 802.11g | 54 | 20 |
| IEEE 802.11n | 450 | 270 |
| IEEE 802.11ac | 866 | 520 |

In light of Table 1 and Table 2, it can be seen that wirelessly transmitting a full resolution x-ray image with 1600×1600 pixels will be very difficult at 8 frames per second and not possible at 30 frames per second. Compressing the image by binning the image would enable wireless transmission at 8 frames per second at the cost of image quality and may be difficult at 30 frames per second. But transmission of a lossy compressed image, such as a JPEG image, can easily be transmitted even at rates faster than 30 frames per second for the highest speed WiFi protocols. In some embodiments, the frame rate during transmission can range from about 12 to about 15 frames per second as an acceptable minimum.

Managing the frame rate and image quality helps provide efficient operation of the portable x-ray device 100 for the operator when analyzing a patient. The x-ray image produced by an x-ray imaging system has an ultimate resolution (ability to resolve a small feature in the object being imaged) that can be determined by the size of the x-ray image produced by the x-ray optical system (determined by the geometric optics of the x-ray source, the distance from the x-ray source to the object, and the distance from the object to the detector) and the number of individual pixels in the x-ray detector. For a typical x-ray imaging device, where the image magnification is small (i.e. on the order of about 1 to about 1.5), the effective image resolution is mostly a function of the detector pixel size. The latest digital x-ray detectors commonly have a pixel size ranging from 70 μm to 100 μm, and therefore require a large number of pixels in order to capture the entire x-ray image, or more than 2,250,000 pixels is common in a single image frame, such as those employed with the various embodiments described herein. Indeed, combining the bit-depth of the image data with the number of pixels, the data per image frame that can be obtained using the portable x-ray device 100 is about 12 times larger than what can be obtained using some conventional systems and methods.

During a fluoroscopy image sequence, the majority of x-ray images are used by the operator for reference or for general position and location information only. At the end of a fluoroscopy imaging sequence, the last x-ray image can be held (i.e., last image hold or LIH) for a more thorough clinical review. The x-ray systems and devices described herein incorporate a lossy compression algorithm during the fluoroscopy imaging sequence, but at the same time display an uncompressed image as the LIH image. During the process, the C-arm can retain the most recent x-ray image(s) in system memory in full resolution. At the end of the fluoroscopy imaging sequence, the last image can then be transmitted regardless of the frame rate since the need to compress data to meet the frame rate requirement has ended. This method will allow the user (or operator) to see a full resolution image for a diagnosis or to check important details since it will be the last image in the sequence or the LIH image that is transmitted at full resolution. In other embodiments, more than just the last full resolution image (i.e., 2 to 5 of the last acquired images) may be transmitted and used in image processing to generate further improvements in image quality of the LIH image. In still other embodiments, the system can be configured to transmit any portion or all of the acquired images at full resolution in the several minutes of idle time that is typically available between fluoroscopy sequences. These full-resolution images could be used for review, to document particular aspects of the medical procedure performed, stored for future uses, or otherwise, depending on the situation.

Once the image sequence has been transmitted and displayed, all or a portion of the images can be stored for later retrieval, as shown in box 530 of FIG. 7. In some embodiments, the entire fluoroscopy full resolution image sequence can be stored on the C-arm for retrieval at a later time. In other embodiments, though, the last full resolution image can be stored on the C-arm for later retrieval. As well, the stored full resolution image sequence can be automatically transmitted at an appropriate data rate to the external computer after the real time compressed image sequence is completed and the x-ray device or C-arm is not engaged in taking a new image sequence.

The portable x-ray devices and methods for imaging described herein exhibit several useful features. The ability for Wi-Fi communications, image compression, and other exposure control and image quality improvement techniques are helpful for the operator when using the portable x-ray devices for x-ray imaging. To obtain a high-speed wireless or WiFi communication with 100 microns (or better) resolution requires transmission of images that contain large amounts of data that must be compressed before transmission. This capability, in turn, requires careful power management of the power from the removable, internal power source (i.e., the battery).

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A real-time imaging method, comprising:
   providing a x-ray imaging device, the x-ray imaging device being portable, and the x-ray imaging device containing an internal power source and an internal power supply;
   capturing a first x-ray image, having a first frame byte size, using the x-ray imaging device;
   compressing the first x-ray image, forming a compressed first x-ray image having a first compressed x-ray image frame byte size, using a compression process performed by a processor located within the x-ray imaging device and then wirelessly transmitting the compressed first x-ray image to a display device;
   capturing a second x-ray image, having a second frame byte size, using the x-ray imaging device;
   compressing the second x-ray image, forming a compressed second x-ray image having a second compressed x-ray image frame byte size, using the processor and then wirelessly transmitting the compressed second x-ray image to the display device, wherein the compressed first x-ray image file has a frame byte size that is less than the frame byte size of the first frame byte size by a factor of 16 or more, and wherein the compressed second x-ray image file has a frame byte size that is less than the frame byte size of the second frame byte size by a factor of 16 or more; and
   displaying the compressed first and compressed second x-ray images on the display device at a frame rate of more than about 8 frames per second, wherein the compressed first and compressed second x-ray images are displayed to generate a motion video sequence.

2. The method of claim 1, wherein the internal power source is a removable battery.

3. The method of claim 1, further comprising capturing, compressing, and transmitting additional images to create a series of images and a series of compressed images forming the motion video sequence.

4. The method of claim 1, wherein the frame rate ranges from 10 to 15 frames per second.

5. The method of claim 1, wherein an operator can operate the x-ray imaging device with a single hand while viewing and manipulating the image results during a medical procedure with the other hand.

6. The method of claim 1, wherein the processor is contained on a FPGA board located internal to the x-ray imaging device.

7. The method of claim 1, wherein a first time between capturing the first x-ray image and displaying the compressed first x-ray image on the display device is less than or 5 seconds.

8. The method of claim 1, wherein, following the wireless transmission of the compressed first x-ray image to a display device, the first x-ray image is wireles sly transmitted to the display device, and further wherein, following the wireless transmission of the compressed second x-ray image to a display device, the second x-ray image is wirelessly transmitted to the display device.

9. The method of claim 3, wherein the display device will retain a latest image set, the latest image set corresponding to the image corresponding to the final compressed image in the series of compressed images.

10. The method of claim 9, where the latest image set includes the last 2 to 5 images of the series of images.

11. The method of claim 7, wherein a first time between capturing the first x-ray image and displaying the compressed first x-ray image on the display device is less than 1 second.

12. An imaging method, comprising:
   providing an x-ray imaging device with a housing containing an internal power source, an internal power supply, and a trigger or foot switch that can be activated while the x-ray imaging device is positioned by hand;
   capturing a first x-ray image, having a first frame byte size, using the x-ray imaging device by activating the trigger;
   compressing the first x-ray image using a compression process performed by a processor, forming a compressed first x-ray image having a first compressed x-ray image frame byte size, the processor located within the x-ray imaging device and then wirelessly transmitting the compressed first x-ray image to a display device;
   capturing a second x-ray image, having a second frame byte size, using the x-ray imaging device;
   compressing the second x-ray image using the processor, forming a compressed first x- ray image having a first compressed x-ray image frame byte size, and then wirelessly transmitting the compressed second x-ray image to the display device, wherein the compressed first x-ray image file has a frame byte size that is less than the frame byte size of the first frame byte size by a factor of 16 or more, and wherein the compressed second x-ray image has a frame byte size that is less than the frame byte size of the second frame byte size by a factor of 16 or more; and
   displaying the first and second x-ray images on the display device at a frame rate of more than 8 frames per second.

13. The method of claim 12, wherein the internal power source is a removable battery.

14. The method of claim 12, further comprising capturing, compressing, and transmitting additional images to create a series of images and a series of compressed images.

15. The method of claim 12, wherein the frame rate ranges from 10 to 15 frames per second.

16. The method of claim 12, wherein an operator can operate the x-ray device with a single hand while viewing and manipulating the image results during a medical procedure with the other hand.

17. The method of claim 12, wherein the processor is contained on a FPGA board located internal to the x-ray device.

18. The method of claim 12, wherein a first time between capturing the first x-ray image and displaying the compressed first x-ray image on the display device is less than 5 seconds.

19. The method of claim 12, wherein, following the wireless transmission of the compressed first x-ray image to a display device, the first x-ray image is wirelessly transmitted to the display device, and further wherein, following the wireless transmission of the compressed second x-ray image to a display device, the second x-ray image is wirelessly transmitted to the display device.

20. The method of claim 14, wherein the display device will retain a latest image in the series of images in full resolution.

21. The method of claim 18, wherein the first time between capturing the first x-ray image and displaying the compressed first x-ray image on the display device is less than 1 second.

22. A hand-held X-ray imaging device, comprising:
a support arm with a housing enclosing an internal power supply and an internal, removable power source, the power source being replaceable and delivering 60 or more X-ray images using a single charge, the support arm being configured to rotate around an object to be analyzed while being held by a support structure;
an X-ray source contained near one end of the support arm;
an X-ray detector contained near the other end of the support arm;
an internal processor and supporting electronics configured to compress an x-ray image by a factor of 16 or more and wirelessly transmit the compressed x-ray image to an external display device; and
a trigger or foot switch that can be activated after the imaging device is properly positioned;
wherein the x-ray device is configured to be removable from the support structure and used in a stand-alone fashion for x-ray imaging.

23. The hand-held X-ray imaging device of claim 22, wherein the processor is contained on a FPGA board located internal to the x-ray imaging device.

* * * * *